(12) United States Patent
Hussain et al.

(10) Patent No.: US 10,952,412 B2
(45) Date of Patent: Mar. 23, 2021

(54) COMPLIANT, LIGHTWEIGHT, NON-INVASIVE, STANDALONE TAGGING SYSTEM FOR MARINE EXPLORATION AND METHOD

(71) Applicant: KING ABDULLAH UNIVERSITY OF SCIENCE AND TECHNOLOGY, Thuwal (SA)

(72) Inventors: Muhammad Mustafa Hussain, Austin, TX (US); Joanna Mohammad Nassar, Thuwal (SA); Sherjeel Khan, Thuwal (SA); Seneca Jackson Velling, Millington, NJ (US)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 0 days.

(21) Appl. No.: 16/620,156

(22) PCT Filed: Jun. 8, 2018

(86) PCT No.: PCT/IB2018/054175
§ 371 (c)(1),
(2) Date: Dec. 6, 2019

(87) PCT Pub. No.: WO2019/012346
PCT Pub. Date: Jan. 17, 2019

(65) Prior Publication Data
US 2020/0137982 A1    May 7, 2020

Related U.S. Application Data
(60) Provisional application No. 62/532,462, filed on Jul. 14, 2017.

(51) Int. Cl.
G08B 23/00 (2006.01)
A01K 29/00 (2006.01)
A61B 5/00 (2006.01)

(52) U.S. Cl.
CPC .......... *A01K 29/005* (2013.01); *A61B 5/6833* (2013.01); *A61B 2503/40* (2013.01);
(Continued)

(58) Field of Classification Search
CPC ............... A01K 29/005; A61B 5/6833; A61B 2503/40; A61B 2560/0242; A61B 2562/0247; A61B 2562/0271
(Continued)

(56) References Cited

U.S. PATENT DOCUMENTS 5,321,268 A    6/1994  Crosby et al.
9,735,893 B1 *  8/2017  Aleksov ............ A61B 5/14546
(Continued)

FOREIGN PATENT DOCUMENTS

WO    2014028084 A2    2/2014
WO    2016030752 A1    3/2016
WO    2016073655 A2    5/2016

OTHER PUBLICATIONS

Block, B.A., et al., "Tracking apex marine predator movements in a dynamic ocean," Nature, vol. 475, Jul. 7, 2011 (Published online Jun. 22, 2011), pp. 86-90.
(Continued)

*Primary Examiner* — Zhen Y Wu
(74) *Attorney, Agent, or Firm* — Patent Portfolio

(57) ABSTRACT

A multi-sensor system for monitoring water parameters, the system including a first metallic layer; a dielectric layer formed on the first metallic layer; a second metallic layer formed on the dielectric layer; a power source electrically connected to the second metallic layer; a computing device
(Continued)

electrically connected to the second metallic layer; and a stretchable outer layer that encapsulates the first metallic layer, the dielectric layer, the second metallic layer, the power source and the computing device. The multi-sensor system is stretchable and flexible.

19 Claims, 11 Drawing Sheets

(52) U.S. Cl.
CPC ............... *A61B 2560/0242* (2013.01); *A61B 2562/0247* (2013.01); *A61B 2562/0271* (2013.01)

(58) Field of Classification Search
USPC ...................................................... 340/573.2
See application file for complete search history.

(56) References Cited

U.S. PATENT DOCUMENTS

| | | | |
|---|---|---|---|
| 2005/0080566 A1 | 4/2005 | Vock et al. | |
| 2008/0007253 A1* | 1/2008 | Takahata | G01D 5/2066 324/207.22 |
| 2008/0173073 A1* | 7/2008 | Downie | H01G 5/0138 73/49.8 |
| 2011/0018725 A1* | 1/2011 | Yang | G01N 33/02 340/627 |
| 2013/0110411 A1* | 5/2013 | Black | G01N 33/18 702/23 |
| 2014/0187681 A1* | 7/2014 | Smith | G01C 9/10 524/21 |
| 2016/0038083 A1* | 2/2016 | Ding | A61B 5/1121 600/388 |
| 2016/0183794 A1* | 6/2016 | Gannon | G01K 13/20 600/549 |
| 2017/0224280 A1* | 8/2017 | Bozkurt | G01L 1/14 |
| 2018/0020982 A1* | 1/2018 | Elsherbini | A61B 5/7405 600/301 |
| 2018/0224382 A1* | 8/2018 | Golombek | G01N 22/04 |
| 2019/0094088 A1* | 3/2019 | Reif | A61B 5/1038 |

OTHER PUBLICATIONS

Bridger, C.J., et al., "The Effects of Biotelemetry Transmitter Presence and Attachment Procedures on Fish Physiology and Behavior," Reviews in Fisheries Science, vol. 11, Issue 1, 2003 (Published online Jun. 24, 2010) pp. 13-34 (23 pages total).
Broadbent, H.A., "A CTD Biotag for Mid-sized Marine Predators," Dissertation submitted to Department of Marine Science, College of Marine Science, University of South Florida, 2012 (Date of Approval Feb. 15, 2012), pp. 1-93 (106 pages total).
Broadbent, H.A., et al., "A Low-Cost, Miniature CTD for Animal-Borne Ocean Measurements," Oceans 2010 MTS/IEEE, 7 pages.
Broderick, A.C., et al., "Effect of tagging marine turtles on nesting behaviour and reproductive success," Animal Behaviour, vol. 58, Issue 3, Sep. 1999, pp. 587-591.
Brown, R.S., et al., "Evidence to Challenge the "2% Rule" for Biotelemetry," North American Journal of Fisheries Management, vol. 19, Issue 3, Aug. 1999 (First Published Jan. 9, 2011), pp. 867-871.
Cooke, S.J., et al., "Biotelemetry: a mechanistic approach to ecology," Trends in Ecology and Evolution, vol. 19, No. 6, Jun. 2004, pp. 334-343.
Cooke, S.J., et al., "Developing a Mechanistic Understanding of Fish Migrations by Linking Telemetry with Physiology, Behavior, Genomics and Experimental Biology: an Interdisciplinary Case Study on Adult Fraser River Sockeye Salmon," American Fisheries Society, Fisheries Magazine, vol. 33, No. 7, Jul. 2008 (First Published Jan. 9, 2011), pp. 321-339.

Costa, D.P., et al., "New Insights into Pelagic Migrations: Implications for Ecology and Conservation," Annual Review of Ecology, Evolution, and Systematics, vol. 43, Dec. 2012 (First published online as a Review in Advance on Aug. 28, 2012), pp. 73-96 (26 pages total).
Duarte, C.M., "Global change and the future ocean: a grand challenge for marine sciences," Frontiers in Marine Science, vol. 1, Article 63, Dec. 2014 (Published Dec. 2, 2014), pp. 1-16.
Geraldi, N.R., et al., "Subtle changes in prey foraging behavior have cascading effects in a shallow estuary," Marine Ecology Progress Series, vol. 427, Apr. 12, 2011, pp. 51-58.
Halpern, B.S., et al., "A Global Map of Human Impact on Marine Ecosystems," Science, vol. 319, Issue 5865, Feb. 15, 2008, pp. 948-952 (6 pages total).
Hammerschlag, N., et al., "Considering the fate of electronic tags: interactions with stakeholders and user responsibility when encountering tagged aquatic animals," Methods in Ecology and Evolution, vol. 5, Issue 11, Nov. 2014, pp. 1147-1153.
Hooker, S.K., et al., "Salinity sensors on seals: use of marine predators to carry CTD data loggers," Deep-Sea Research Part I, vol. 50, Issue 7, Jul. 2003, pp. 927-939.
Hoolihan, J.P., et al., "Evaluating post-release behaviour modification in large pelagic fish deployed with pop-up satellite archival tags," International Council for the Exploration of the Sea (ICES) Journal of Marine Science, vol. 68, No. 5, May 2011 (Advance access publication Mar. 15, 2011), pp. 880-889.
Humphries, N.E., et al., "Foraging success of biological Lévy flights recorded in situ," PNAS, vol. 109, No. 19, May 8, 2012, pp. 7169-7174.
Hussain, A.M., et al., "CMOS-Technology-Enabled Flexible and Stretchable Electronics for Internet of Everything Applications," Advanced Materials, vol. 28, Issue 22, Jun. 8, 2016 (Published online Nov. 26, 2015), pp. 4219-4249.
Hussey, N.E., et al., "Aquatic animal telemetry: A panoramic window into the underwater world," Science, vol. 348, Issue 6240, Jun. 12, 2015, pp. 1255642-1-1255642-10 (12 pages total).
Jepsen, N., et al., "A brief discussion on the 2% tag/bodymass rule of thumb," Aquatic telemetry: advances and applications, Proceedings of the Fifth Conference on Fish Telemetry held in Europe, Ustica, Italy, Jun. 9-13, 2003, pp. 255-259.
Jones, T.T., et al., "Calculating the ecological impacts of animal-borne instruments on aquatic organisms," Methods in Ecology and Evolution, vol. 4, Issue 12, Dec. 2013, pp. 1178-1186.
Miller, K.M., et al., "Genomic Signatures Predict Migration and Spawning Failure in Wild Canadian Salmon," Science, vol. 331, Issue 6014, Jan. 14, 2011, pp. 214-217 (5 pages total).
Nassar, J.M., et al., "From stretchable to reconfigurable inorganic electronics," Extreme Mechanics Letters, vol. 9, Part 1, Dec. 2016 (Available online May 6, 2016), pp. 245-268.
Shaikh, S.F., et al., "Freeform Compliant CMOS Electronic Systems for Internet of Everything Applications," IEEE Transactions on Electron Devices, vol. 64, No. 5, May 2017 (Date of publication Jan. 16, 2017; date of current version Apr. 19, 2017), pp. 1894-1905.
Shorter, K.A., et al., "Drag of suction cup tags on swimming animals: Modeling and measurement," Marine Mammal Science, vol. 30, Issue 2, Apr. 2014, pp. 726-746.
Talley, L.D., "Salinity Patterns in the Ocean," Encyclopedia of Global Environmental Change, vol. 1, The Earth system: physical and chemical dimensions of global environmental change, 2002 (pp. 629-640), pp. 1-11 (12 pages total).
University of St. Andrews, "SMRU Instrumentation," Scottish Oceans Institute, CTD Oceanography SRDL (Argos), 2017, http://www.smru.st-and.ac.uk/Instrumentation/CTD/, Data Sheet, 1 page.
Walker, K.A., et al., "A review of the effects of different marking and tagging techniques on marine mammals," Wildlife Research, vol. 39, No. 1, Jan. 2012 (Published online Dec. 21, 2011), pp. 15-30 (17 pages total).
International Search Report in corresponding/related International Application No. PCT/IB2018/054175, dated Nov. 15, 2018.

(56) References Cited

OTHER PUBLICATIONS

Written Opinion of the International Searching Authority in corresponding/related International Application No. PCT/IB2018/054175, dated Nov. 15, 2018.

* cited by examiner

COMPLIANT, LIGHTWEIGHT, NON-INVASIVE, STANDALONE TAGGING SYSTEM FOR MARINE EXPLORATION AND METHOD

CROSS REFERENCE TO RELATED APPLICATIONS

This application is a U.S. National Stage Application of International Application No. PCT/IB2018/054175, filed on Jun 8, 2019, which claims priority and benefit from U.S. Provisional Patent Application No. 62/532,462, filed on Jul. 14, 2017, for "Compliant Lightweight Non-Invasive Standalone 'Marine Skin' Tagging," the content of which is incorporated in its entirety herein by reference.

BACKGROUND

Technical Field

Embodiments of the subject matter disclosed herein generally relate to multi-sensory equipment for measuring various parameters of a marine environment, and more specifically, to methods and systems for making such multi-sensory equipment and attaching it to various marine organisms.

Discussion of the Background

Marine ecosystems are experiencing worldwide anthropogenic-driven change, including extensive overfishing, run-off population, pollution, and increasing global warming (see Duarte (2014) and Halpern (2008)). The ability to monitor and record various environmental and population parameters allows greater understanding of human impact, enhanced mitigation strategies, and the opportunity for systematic feedback to shape policy implementation. In this context, rapid advancements in electronic tagging and tracking tools have enabled the research community to remotely study a broad array of variables, to monitor marine ecosystem health, and how changes in the environment affect marine animals. Electronic tagging of marine life has provided information on animal behavior, environmental conditions and geographical position (see, Block (2011), Costa (2012), Cooke (2008), Humphries (2012), and Miller (2011)). At the same time, marine tags should not weight more than 2% of the dry body weight of the tagged animal to maintain normal behavior, physiology and survival of the tagged individual (see, Bridger (2003) and Jepsen). Yet, most devices in the market are unsuitable for young specimens, invertebrates, or small species, because the tag exceeds this tenet (see, Cooke (2004) and Brown (1999)).

While many studies have focused on larger species, such as Cetaceans, Dolphins, and Sirenians, attachment methods for the existing monitoring systems are invasive. As an example, standard attachment techniques include using a shotgun or crossbow to insert tags into the animal's tissue, or cutting tools and bolts to fix a tag to the dorsal fins (see Walker (2012)).

Such techniques often lead to infection of the tagged area, or over sensitivity of the skin. For other animals, internal or external sensor attachment can be done through capture and short term sedation (see Geraldi (2011)). However, in both cases, the invasiveness of the procedures could stress the tagged individuals and compromise the animal's health. Several studies have been conducted analyzing the repercussions of marine tagging, and they showed that the extra carried weight and the design of the tag can negatively affect diving patterns, mating, nesting behavior, and swimming drag (see Broderick (1999), Shorter (2014), Hammerschlag (2014), Jones (2013)).

Therefore, the current size of marine sensors limit the diversity of species that could be studied, and further technological developments are required to provide more comfortable animal-friendly tagging devices that are not invasive and can conform to the animal's morphology.

Despite the advances made on marine electronic tagging research (see Broadbent (2010), Broadbent (2012), and SMRU-Instrumentation), there are still major areas of the marine sensors that need improvement, including prolonged tag lifetime, increased sensor capabilities, better attachment techniques, and tag conformity to promote natural and unrestricted movement. Marine tag design should include animal comfort without compromising the performance, data validity and endurance of the system. Also, the sensor cost should not exceed current market standards to be considered commercially effective.

Therefore, there is a need for a compliant and stretchable marine tag, which should be lightweight, non-invasive, durable, bio-compatible and capable of monitoring the marine environment while retaining high performance and resolution standards.

SUMMARY

According to an embodiment, there is a multi-sensor system for monitoring water parameters. The system includes a first metallic layer; a dielectric layer formed on the first metallic layer; a second metallic layer formed on the dielectric layer; a power source electrically connected to the second metallic layer; a computing device electrically connected to the second metallic layer; and a stretchable outer layer that encapsulates the first metallic layer, the dielectric layer, the second metallic layer, the power source and the computing device. The multi-sensor system is stretchable and flexible.

According to another embodiment, there is a multi-sensor system for monitoring water parameters. The system includes a temperature sensor for measuring a temperature of an ambient; a pressure sensor for measuring a pressure of the ambient; a salinity sensor for measuring a salinity of the ambient; a computing device having a temperature sensing unit configured to read a temperature from the temperature sensor, a pressure sensing unit configured to read a pressure from the pressure sensor, a salinity sensing unit configured to read a salinity from the salinity sensor, a memory configured to store the temperature, the pressure and the salinity, and a low power Bluetooth transmitter configured to send the stored temperature, pressure and salinity to an external device; and a power source for supplying power to the computing device. The multi-sensor system is stretchable and flexible.

According to yet another embodiment, there is a method of forming a multi-sensor system for monitoring water parameters. The method includes forming a first metallic layer, forming a dielectric layer on the first metallic layer, forming a second metallic layer on the dielectric layer, attaching a power source to the second metallic layer, attaching a computing device to the second metallic layer, and encapsulating in a stretchable outer layer the first metallic layer, the dielectric layer, the second metallic layer, the power source and the computing device. The multi-sensor system is stretchable and flexible.

BRIEF DESCRIPTON OF THE DRAWINGS

The accompanying drawings, which are incorporated in and constitute a part of the specification, illustrate one or more embodiments and, together with the description, explain these embodiments. In the drawings.

DETAILED DESCRIPTION

The following description of the embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to a marine skin multi-sensor system that includes pressure, temperature and salinity sensors. However, other type of sensors may be added to the system.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

With advances in state-of-the-art miniaturized electronics and capitalizing on the emergence of flexible and stretchable form factors to integrate life, device, data and processes through Internet of Everything (see Nassar (2016), Shaikh (2017), and Hussain (2015)), a waterproof ultra-lightweight (in one application the system weights less than 2.4 grams), fully conforming (physically flexible and stretchable), stand-alone wireless multi-sensory (conductivity, temperature, depth) "Marine Skin" sensor system is built. In one application, a size of this multi-sensor system is 55 mm×55 mm×0.3 mm. In one embodiment the length may be between 25 and 75 mm and the width may be between 25 and 75 mm. This ultra-light weight multi-sensor system has non-invasive application, high performance multi-sensing, constant data logging with significantly lower cost. Integrated arrays of temperature, pressure and conductivity sensors may simultaneously monitor the animal's diving patterns, and the surrounding environmental conditions. Such integrated arrays are now discussed with reference to the figures.

Existing multi-sensory platforms allow data collection which can predict changes in behavior, population size, and range/distribution of marine species. However, available designs do not respond to changes in an animal's air/water flow dynamics (see Hussey (2015)). Conductivity (i.e., salinity), temperature and depth provide a basic description of the ocean's environment, allowing characterization of water masses and the niche used by marine animals.

Figure 1:
FIG. 1 illustrates various known devices, which can be attached to marine animals for monitoring water parameters.

Hence, efforts in the development of marine sensors are mainly focused on these environmental parameters (see Hooker (2003)). Yet, one of the greatest challenges for effective monitoring and experimentation is the physical size of equipment, weight, and attachment invasiveness. In this regard, FIG. 1 illustrates various known marine sensors and their characteristics. It is noted that most of the sensors are heavier than the recommended 2% threshold discussed above. Thus, these sensors make very uncomfortable the life of those animals to which they are attached. For those marine sensors that are below the 2% threshold discussed above, their method for attaching the sensor to the marine animals is invasive, which is also undesirable.

Figure 2:
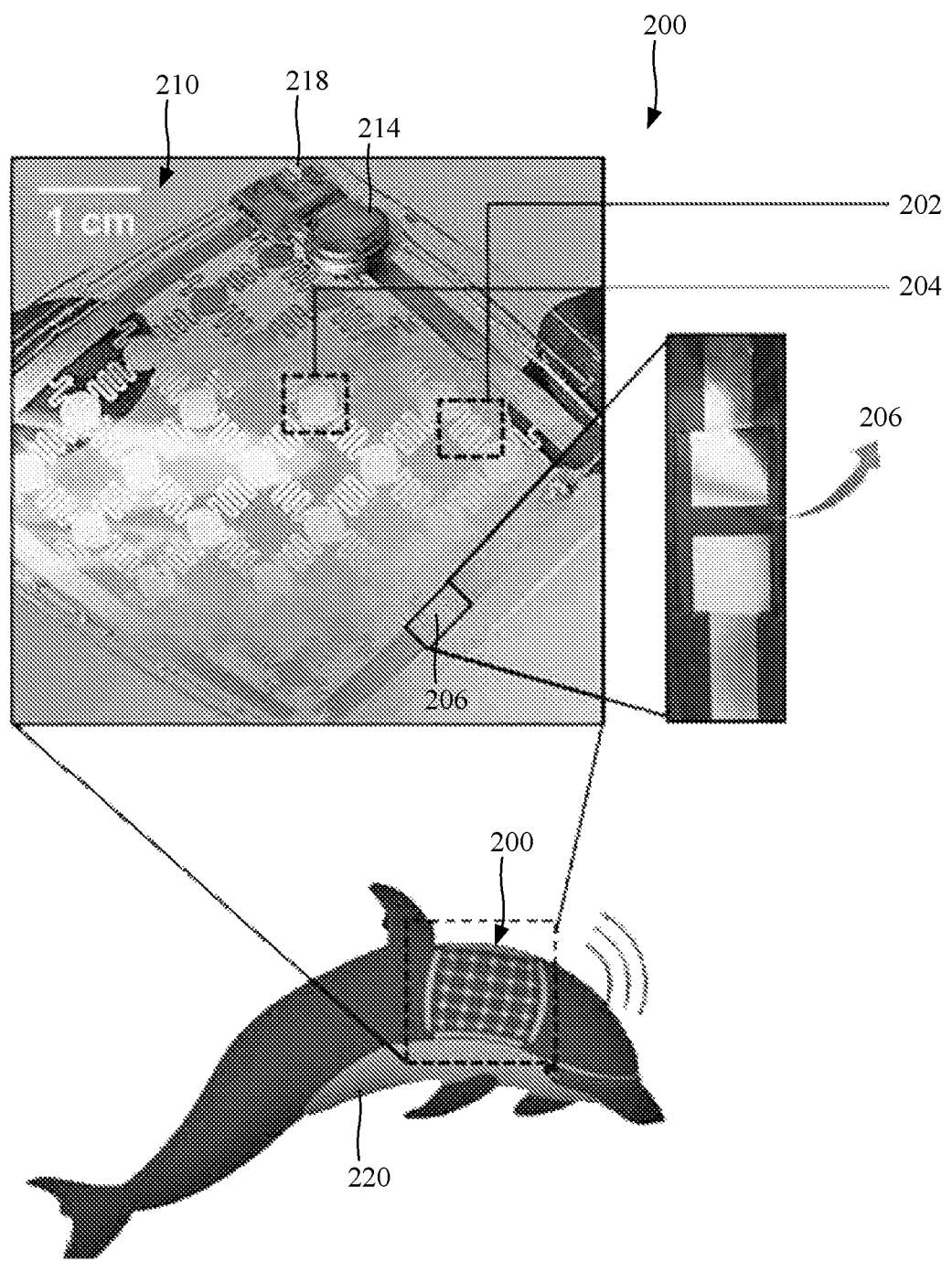
FIG. 2 illustrates a new multi-sensor system that is attached to marine life organisms for monitoring various parameters of the water.

With these goals in mind, the present inventors have designed a multi-sensory system 200, see FIG. 2, that includes at least one temperature sensor 202, at least one pressure sensor 204, and at least one salinity sensor 206. These sensors are located in a packaging material 210, which is later discussed in more detail. The packaging material may also house a power source 214 and a computing device 218. Multi-sensory system 200 may be attached, as discussed later, to the skin of a mammal 220 or other marine life organism through a procedure that is not harmful to the organism (e.g., by gluing). The computing device 218 receives the measured information from the various sensors and store it in a local memory. When a condition is triggered (e.g., the sensor is at the water surface), the computing device 218 may transmit the stored information to an external harvester device (not shown), for example, using a low consumption Bluetooth transceiver located in the computing device. The harvester device may be a smartphone, laptop, tablet or other similar device.

Because effective marine sensors need to survive the particularly corrosive saline aqueous environment (35-40 practical salinity unit, PSU) and maintain high sensitivity and repeatability, the selected packaging material 210 has been selected to be a compliant packaging material that takes into consideration biocompatibility, toxicology, cost, endurance in saline environments, temperature and pressure working ranges, and degradation with time. The selected packaging material 210 complies with the soft elasticity of the hosting surface, minimizing any kind of discomfort caused when the system is placed on the asymmetric surface (often soft) of marine animals, and supporting freedom of movement without any restrictions.

In one embodiment, the "Marine Skin" multi-sensory system used on Polydimethylsiloxane (PDMS) Sylgard 184™, as the conformal packaging material, among other available flexible and stretchable polymeric counterparts (e.g. Ecoflex®). The PDMS is hydrophobic, non-toxic and non-irritating to the skin, does not decompose under high heat or halogenation, and unlike Ecoflex, no major reduction concern is seen under minimal biofouling. In addition, PDMS is effective for the current cause due to its ease of flow integration and compatibility with CMOS processes using state-of-the-art industry equipment. The PDMS may be considered to be a water proof, biocompatible soft encapsulating material. Other materials may accomplish this function.

Figure 3:
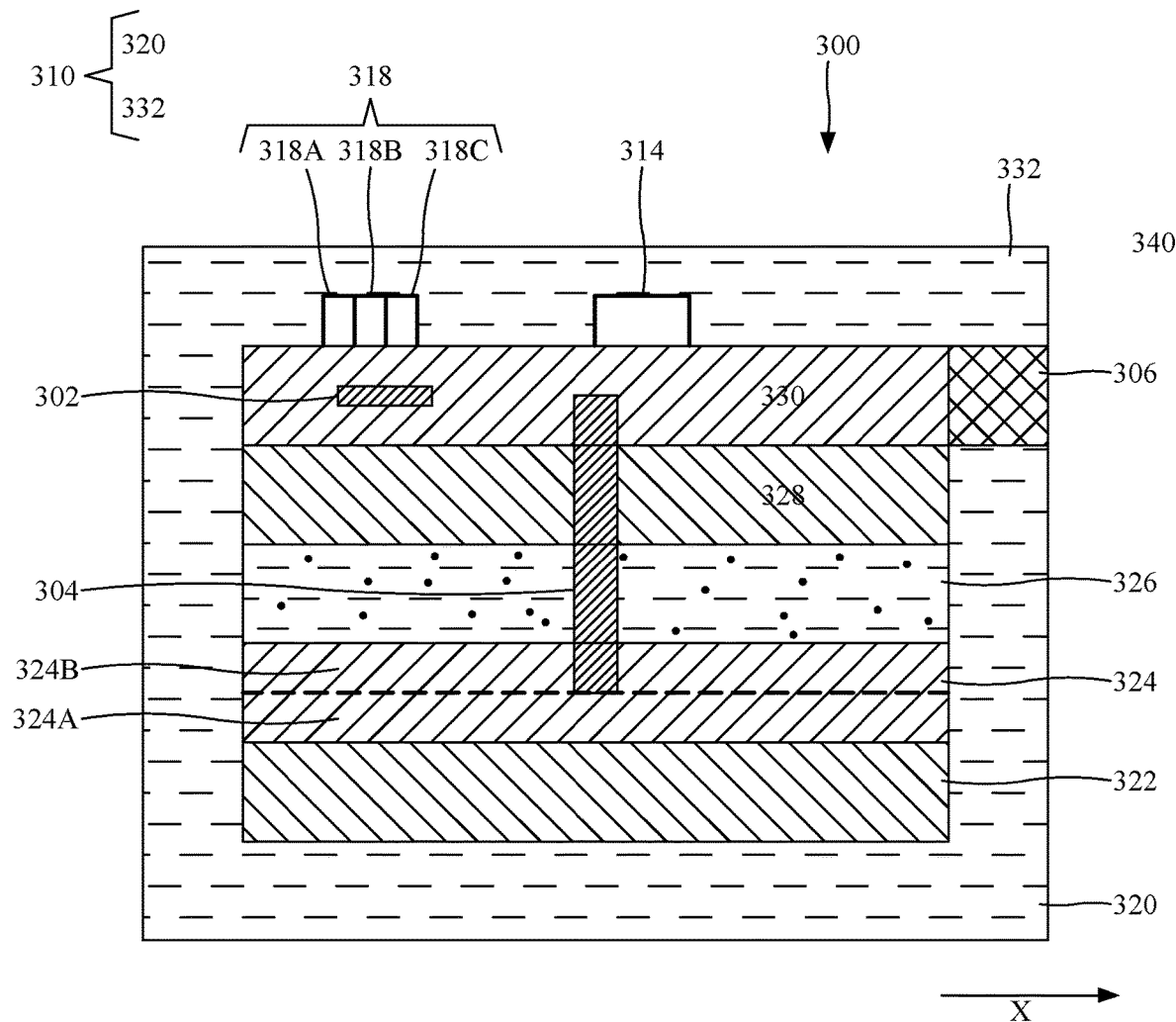
FIG. 3 illustrates the various elements of a multi-sensor system that is flexible and stretchable.

FIG. 3 shows a cross-section of a multi-sensor system 300. It includes a first stretchable layer 320, which is part of the packaging material 210 (also called stretchable outer layer) shown in FIG. 2, a first flexible layer 322, a first metallic layer 324, a dielectric layer 326, a second flexible layer 328, a second metallic layer 330, and a second stretchable layer 332 (also part of the packaging material 210), each layer formed on top of the other in the order indicated in the figure. The first and second stretchable layers 320 and 332 form the packaging material 310 (i.e., a stretchable outer layer that encapsulates all the other layers), discussed as element 210 in FIG. 2. According to this embodiment, a layer or device or system is considered to be stretchable if a length of the layer, e.g., along a longitudinal axis X, can increase between 5 and 25% of its original length when a force is applied, without damaging the layer. The first and second stretchable layers 320 and 332 may be made, in one embodiment, out of PDMS. Other materials may be also be used. A thickness of the first and second stretchable layers may be between 100 and 200 µm. In one embodiment, the first stretchable layer has a thickness of 100 µm and the second stretchable layer has a thickness of 150 µm. Other dimensions may be used.

The first flexible layer 322 is formed, in one application, directly on top of the first stretchable layer 320. The first flexible layer 322 may not be stretchable. In one application, the first flexible layer 322 may have a thickness of 10 µm and may be made of Polyimide. Other thickness and materials may be possible. The second flexible layer 328 may have the same size and composition as the first flexible layer 322. The second flexible layer 328 is formed, in one embodiment, directly on top of the dielectric layer 326.

The first metallic layer 324 is formed, in one embodiment, directly on top of the first flexible layer 322. The first metallic layer 324 may include two or more sub-layers. For example, in one embodiment, the first metallic layer 324 includes a first layer 324A of titanium (Ti) and a second layer 324B of gold (Au). In one embodiment, the first layer 324A of Ti has a thickness of 10 nm and the second layer 324B of Au has a thickness of 180 nm. Other combinations of metals may be used.

The dielectric layer 326 is formed, in one embodiment, directly on top of the first metallic layer 324. The dielectric layer 326 can be made of any dielectric material that is appropriate for forming the dielectric of a capacitor because this layer, after being patterned as discussed later, would serve as part of one or more capacitors that form the pressure/depth sensor. Further, the dielectric material should be a pressure sensitive material, i.e., it changes at least one size when a pressure acts on this material. In one application, the dielectric layer 326 is formed of PDMS or another pressure sensitive rubber. In one application, a thickness of the dielectric layer 326 is about 50 µm.

The second metallic layer 330 is formed, in one embodiment, directly on top of the second flexible layer 328. The second metallic layer 330 may have the same composition as the first metallic layer 324 and the same sizes. However, other materials and sizes may be used.

One or more temperature sensors 302 (202 in FIG. 2) are formed in the second metallic layer 330 through a process that is discussed later. The temperature sensor includes a thin-film based resistive temperature detector (RTD), where a temperature change is reflected through a linear change in the sensor's resistance. The temperature sensor structure may include, as illustrated in FIG. 2, a wavy (serpentine) Ti/Au (e.g., 10 nm/180 nm thickness layers) metal structure. The adopted serpentine design maximizes the area for thermal exposure, but also minimizes strain induced by resistance changes. In addition, the serpentine design makes the entire metallic layer stretchable. The sensitivity of the temperature sensor 302 will be reflected through the temperature coefficient of resistance (TCR) which is specific to the material used. A simple thin film RTD design is chosen in one embodiment because it does not require high power supply, and shows to be very repeatable with high linearity (e.g., accuracy of $<\pm 0.1°$ C.) and long term stability and durability. In one embodiment, the second metallic layer includes an array of temperature sensors that form a net as shown in FIG. 2. Each temperature sensor may be formed on a side of a square (or other shapes) and plural squares form the net.

For the depth detection, a pressure sensor 304 is constructed between the first and second metallic layers 324 and 330 to measure the hydrostatic pressure. The hydrostatic pressure of submerged objects is a measure of the buoyant force uplifting the object. Relative changes in hydrostatic pressure $P_{hydrostatic}$ scales linearly as given by equation:

$$P_{hydrostatic} = \rho \times g \times h \quad (1)$$

where 'ρ' is the water density, 'g' is the Earth-surface gravitational acceleration, and 'h' is the measure of depth of the object (or height from the surface of the water). A total pressure 'P' experienced by the object underwater is the sum of partial pressures, $P=P_0+P_{hydrostatic}$, where $P_0$ (atmospheric/barometric pressure) at sea level is about 1.01325 bar=14.696 psi on average. Most conventional pressure sensors have high sensitivity, but limited operating range, precluding their use in marine sensors. The sensors must sustain an approximate 10 kPa per meter depth total pressure increase underwater, where at 100 m depth the pressure is 10 times atmospheric pressure. For this reason, a capacitive pressure sensor using parallel plate capacitive structure was chosen. The pressure sensor 328, which is schematically illustrated in FIG. 3, thus has the two plates made of portions of the first and second metallic layers 324 and 330 (e.g., using Ti/Au (10 nm/180 nm) as top and bottom electrodes) and, for the compressive pressure-sensing dielectric rubber, a portion of the dielectric layer 326 (e.g., PDMS of about 50 µm thick). In one embodiment, as illustrated in FIG. 2, an array of pressure sensors are formed between the first and second metallic layers. The pressure sensors may be located at an intersection of four different temperature sensors, i.e., at the corners of each square of the net shown in FIG. 2.

Capacitive sensors offer advantages in the frequency response, repeatability with use (longer shelf-life), and a linear relationship with pressure. In one application, the thickness of the PDMS dielectric is optimized by balancing two criteria: (1) flexibility and stretchability, (2) and signal saturation. Thinner PDMS layers can be more flexible, but will lead to faster saturation of the sensor under extreme pressures, whereas thicker layers of PDMS can withstand higher pressures as they have more room for compression/deformation, but they can be limited with their flexibility. In one application, considering a curing temperature of T=100° C. for the PDMS layer (which is slightly higher than a curing temperature disclosed later in regard to a method of making the multi-sensor system), the PDMS would be roughly characterized by a Young's modulus of E~2 MPa, with an average failure load of 112.5 kN, while the compressive properties are characterized by a compressive modulus of 148.9 MPa. To derive the additional mechanical properties of shear modulus and bulk modulus for the cured PDMS, equation (2) below relates the Young's modulus to both the shear and bulk moduli via Poisson's ratio (v) by:

$$E=2G(1+v)=3K(1-2v) \quad (2)$$

Considering the Poisson's ratio of Sylgard 184 is ranging from 0.45-0.5, the hardness properties of PDMS cured at T=100° C. are approximately defined by shear modulus of G=0.68 MPa and bulk modulus by K=3.42 MPa.

Figure 4:
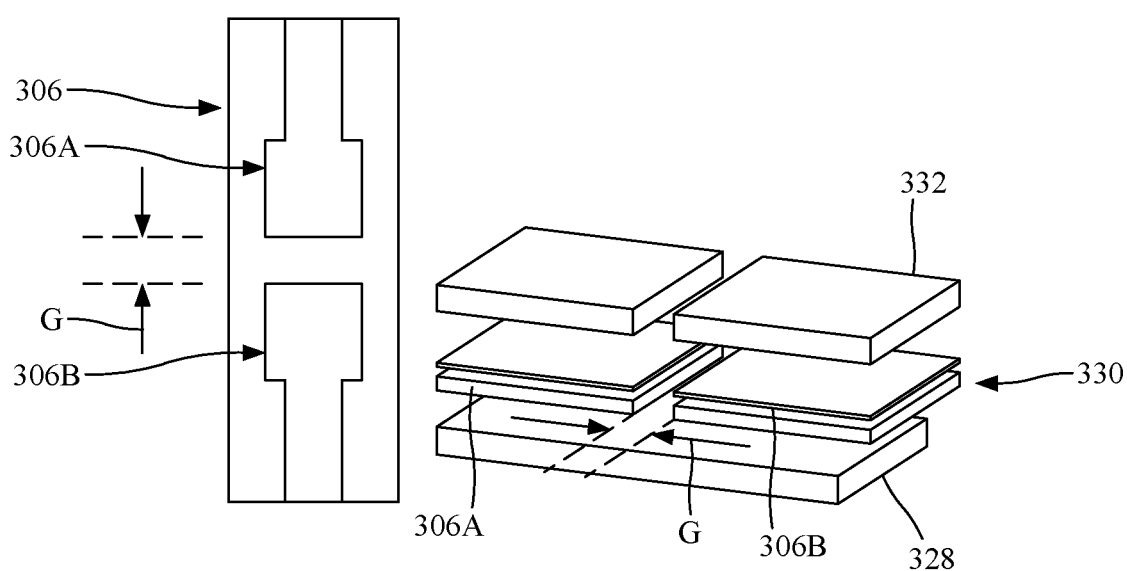
FIG. 4 illustrates a salinity sensor of the system of FIG. 3.

For the salinity sensor 306, the multi-sensory system 300 uses the concept of conductivity measurement. The salinity sensor measures the ability of a solution to conduct an electric current between two electrodes. Thus, such a structure includes two electrodes (e.g., made of Ti/Au) separated by a gap (in one application the gap is 2 mm, but other values may be used), as shown in FIG. 4. Note that a part of the PDMS 332 that is formed over the second metallic layer 330 (which includes the salinity sensor 306) has been removed so that the two electrodes 306A and 306B are in direct contact with the water. In this regard, note that FIG. 3 shows the salinity sensor 306 to be in direct contact with the environment 340. The gap G between the two electrodes 306A and 306B extends in the plane of the second metallic layer 330. The two electrodes 306A and 306B shown in FIG. 4 are formed in the second metallic layer 330 in FIG. 3. In one embodiment, one electrode is electrically connected to a temperature sensor (see FIG. 2) and the other electrode is electrically connected to the computing device 218 or power source 214.

In presence of an ionic conductive solution (such as sea water), a resistance between the two electrodes 306A and 306B decreases as the solution becomes more conductive (viz. higher salinity content).

Returning to FIG. 3, the multi-sensor system 300 may also include a power source 314 that is electrically connected to the second metallic layer 330. The entire power source 314 is covered by the second stretchable layer 332 to protect if from the negative influences of the environment (e.g., corrosive action of the seawater). The power source 314 may be, for example, a coin cell battery. The coin cell battery may be a 3V coin cell battery. In one embodiment, the power source is a piezoelectric element that generates energy due to the changes in ambient pressure as the marine animal moves up and down. Other mechanism may be used to generate power.

The multi-sensor system 300 may also include a computing device 318, also formed/attached to the second metallic layer 330. The computing device 318 is encapsulated in the second stretchable layer 332 to prevent damage from the environment. While FIG. 3 shows the computing device 318 formed as a unit that is electrically attached/connected to the second metallic layer 330, in one embodiment it is possible to have the components of the computing device (e.g., transistors, resistors, capacitors, diodes, etc.) formed in the first and second metallic layers 324 and 330 or even formed in additional metallic layers (not shown in the figure). In other words, the components of the computing device may be distributed over the system 300 in one or more layers.

The computing device 318 may include a Programmable System-on-Chip (PSoC) 318A with integrated Bluetooth transceiver 318B, which uses a low power Bluetooth technology (BLE)). PSoC 318A, which may include passive components and antenna, may be mounted on a 10 mm×10 mm Printed Circuit Board (PCB). The PSoC may have a built-in Op-Amps and capacitance sensing elements, thereby eliminating the need of any external IC other than the PSoC. BLE has a wide bandwidth and lower power consumption than WiFi on the expense of a reduced range. An algorithm run on the processor of the computing device is capable to take readings from all three sensor types, and store their values in the PSoC's internal flash memory 318C (e.g., 256 KB). With a logging frequency of 1 Hz, system 300 operates from 1.7-3.3 V, and thus the power supplied by a 3V coin cell battery is enough. To reduce power consumption, the algorithm was designed in such a way that the system reads data from sensors in <50 ms and goes to sleep during each logging cycle. The transceiver is kept off while in water and only when the system senses that the animal is out of water (using readings from both the pressure and salinity sensor), the transmission mode becomes active. The steady current consumption in sleep mode may be 50 µA, active (reading sensors) mode may be 8 mA, and wireless transmission mode may be 12 mA.

As the resistive sensors are made out of gold, conventional methods of detecting changes in resistance, like resistive dividers and Wheatstone bridge, consume large currents, thereby reducing the operational lifetime of the system. Sometimes, complex interface circuits are needed to get readings from resistive sensors which increases the size and complexity of the interface. By using an internal Op-Amp of PSoC, a current source is created that feeds a fixed small amount of current (e.g., less than 300 µA) directly into the resistive sensors and the resulting voltage changes were detected by inbuilt analog-to-digital convertor (ADC). This approach, compared to conventional methods, consumes 10 times less power and no additional reference resistors are needed. Traditionally, an additional integrated circuit (IC) of Capacitance-to-Digital convertor is used to read capacitance of capacitive sensors, but the PSoC's engrained Capsense™ technology is configured to directly read the capacitance of the pressure sensors.

By making intelligent use of the PSoC internals, system 300 is able to avoid the need of using any additional components other than the BLE chip itself for both capacitive and resistive readings, and in-turn reduced the power consumption drastically.

Figure 5:
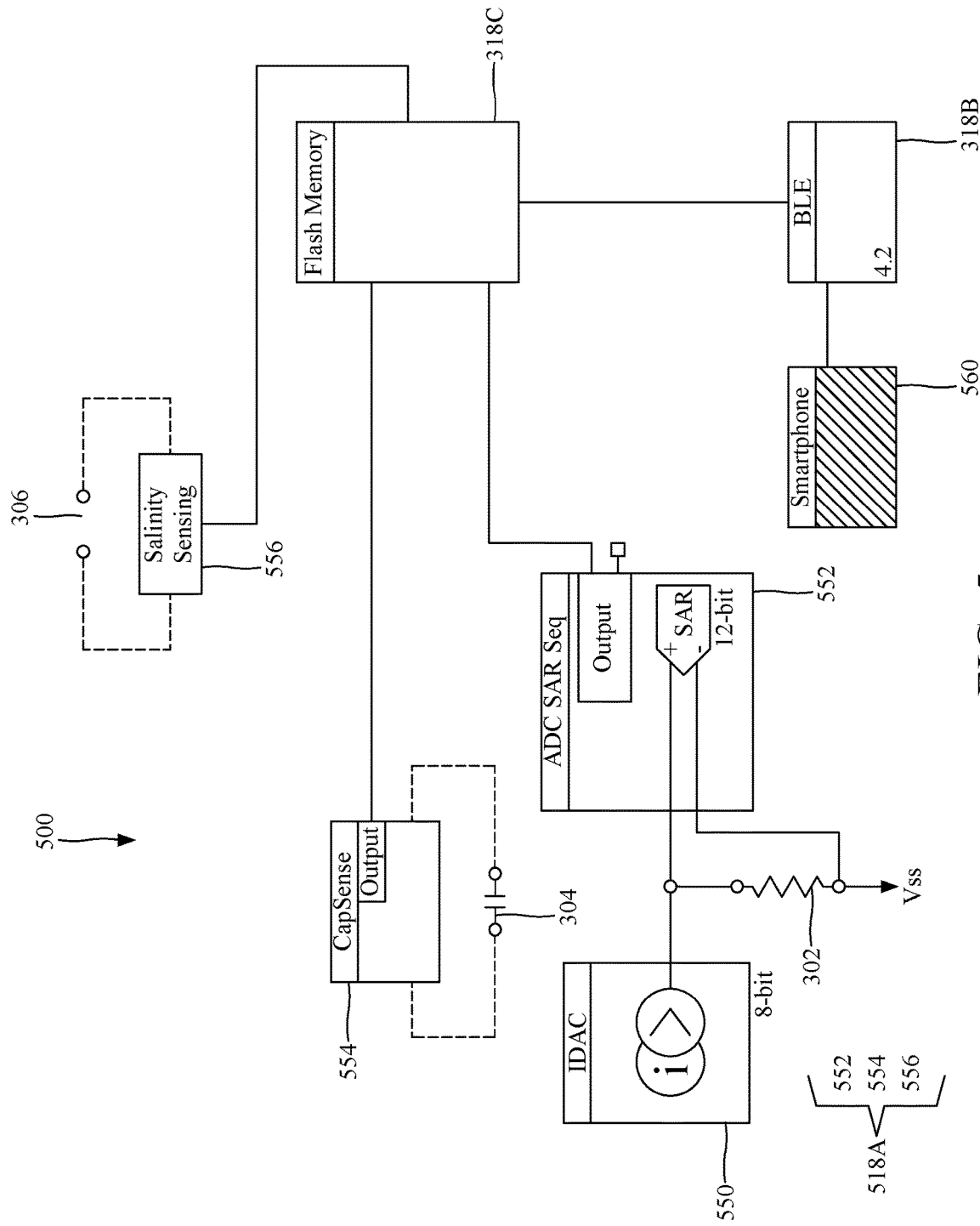
FIG. 5 illustrates physical and logical elements of a multi-sensor system that is flexible and stretchable.

FIG. 5 is a schematic diagram of a multi-sensor system 500 that shows both physical and logical components and how they interact to collect the temperature, pressure and salinity data. System 500 includes at least one temperature sensor 302, at least one pressure sensor 304, and at least one salinity sensor 306. Those skilled in the art would understand that more sensors of the same type may be present. Temperature sensor 302 is associated with a temperature sensing unit 552, hosted by the PSoC microcontroller 518A. Temperature sensing unit 552 is connected to the temperature sensor 302 and current source 550 (which is part of the PSoC microcontroller 518A) and includes software instructions for reading the voltage and current across the temperature sensor 302. Based on the resistance calculated from the sensed voltage and current, a temperature of the ambient is determined and stored in storage element 318C, which can be a flash memory. Pressure sensing unit 554 (which is also part of the PSoC microcontroller 518A) is connected to pressure sensor 304 for sensing a capacitance of the sensor. The capacitance is then translated into a distance between the two plates of the capacitor forming the pressure sensor 304, which is correlated with a depth of the pressure sensor in water. In this way, the pressure and/or depth of the sensor is determined. The pressure and/or depth is then stored in the storage element 318C. Similarly, a salinity sensing unit 556 (which is also part of the PSoS microcontroller 518A) is connected to salinity sensor 306 and determine a salinity value, as discussed above. This value is then stored in the storage element 318C.

Data may be continuously logged at 1 Hz in the PSoC's internal flash memory 318C, and only when the animal emerges out of water, data is wirelessly collected, via BLE, at a harvesting device 560 (e.g., a smartphone) as depicted in FIG. 5.

Figure 6A:
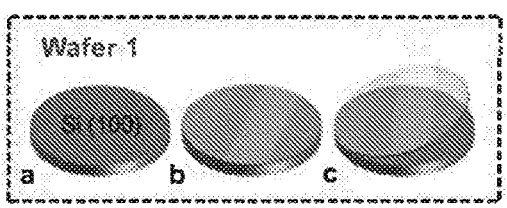
FIGS. 6A-6C illustrate various steps of forming a multi-sensor system and FIG. 6D illustrates the resultant multi-sensor system.
Figure 6B:
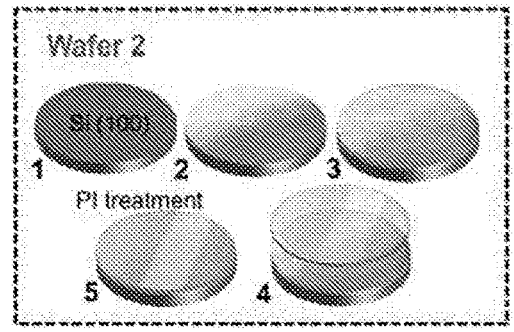
Figure 6C:
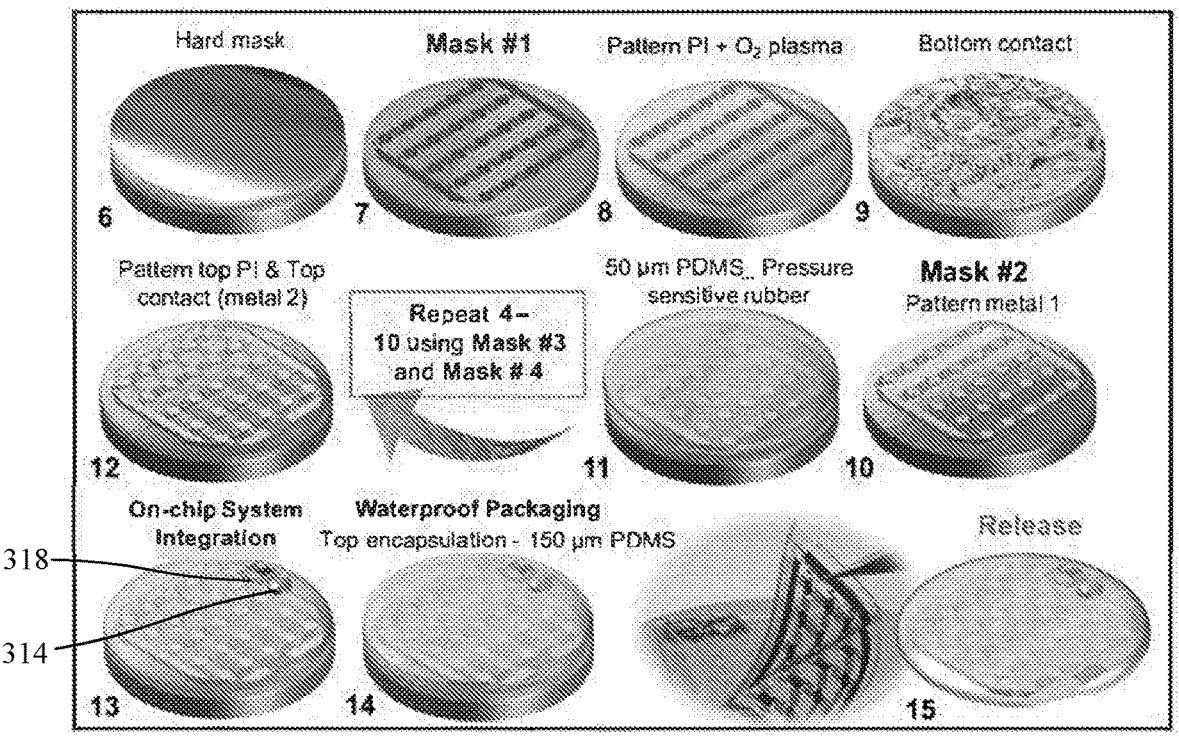
Figure 6D:
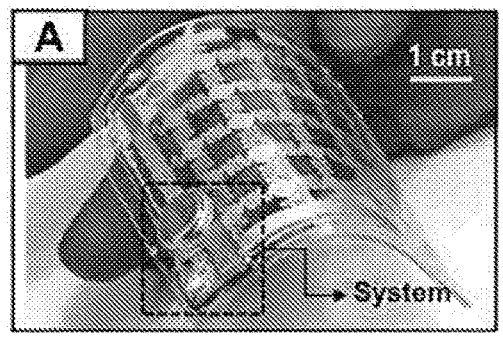
Figure 7A:
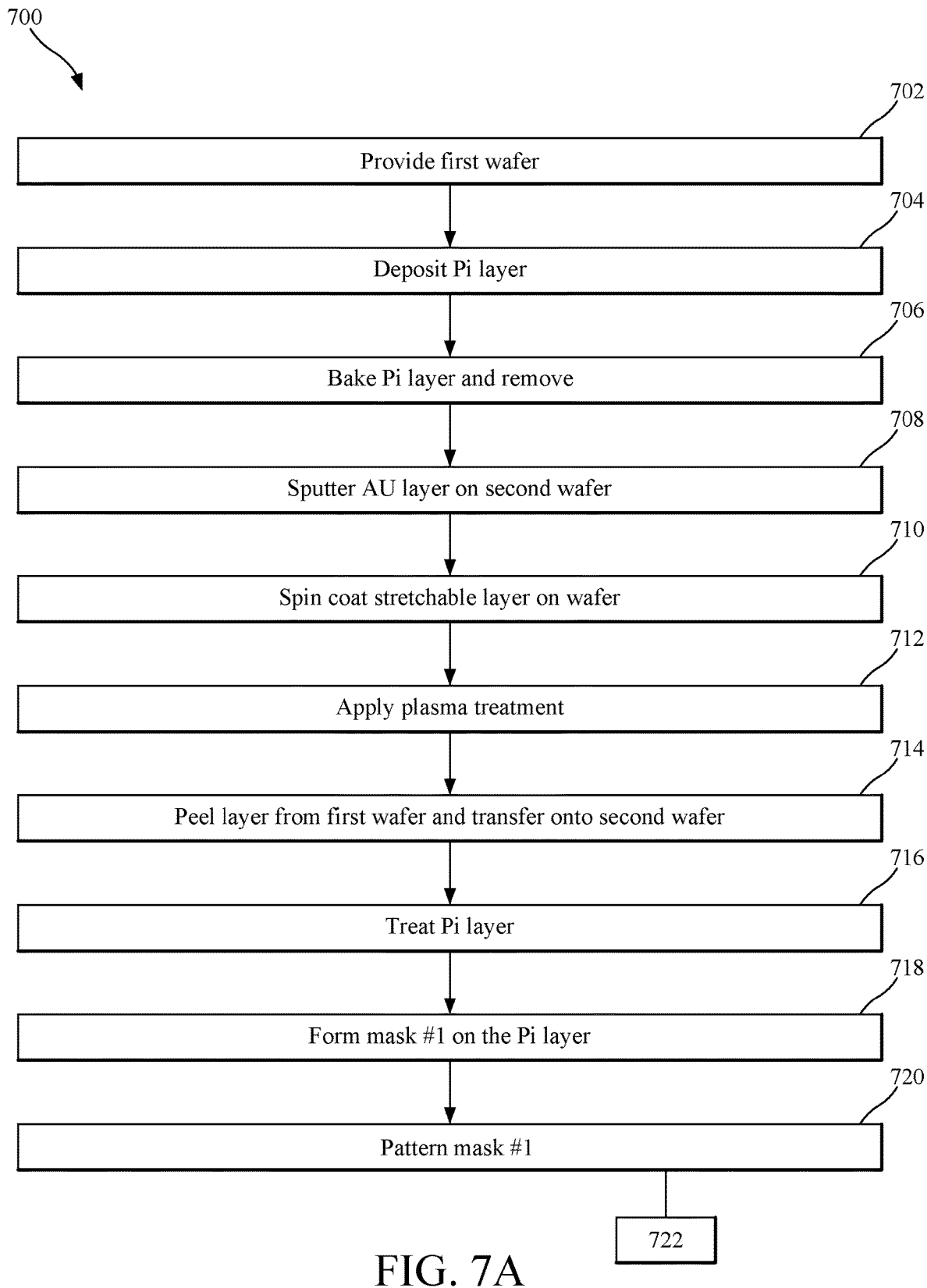
FIGS. 7A and 7B illustrate the steps of a method for forming a multi-sensor system that is flexible and stretchable.
Figure 7B:
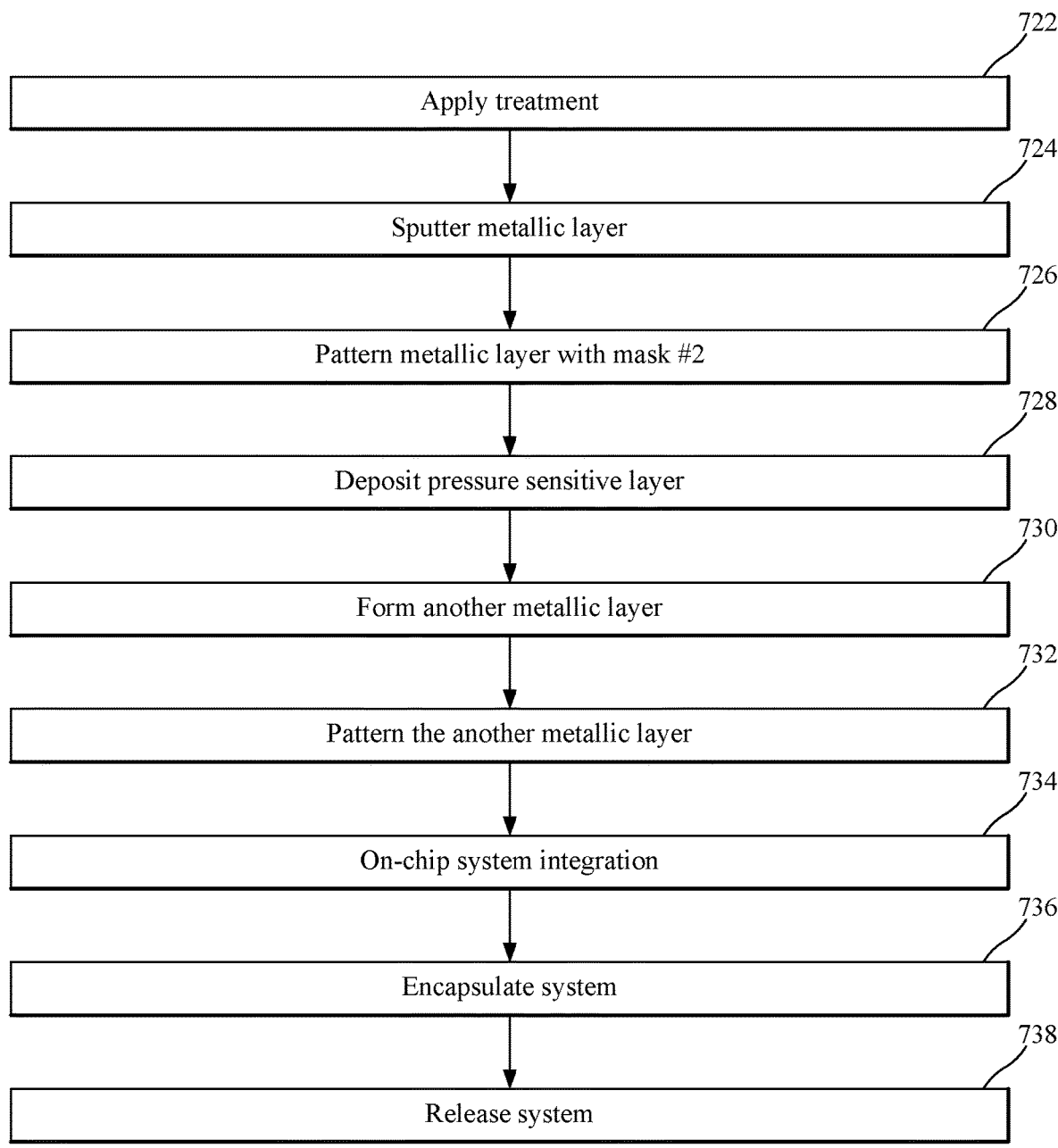

A method of forming the system 300 or 500 is now discussed with regard to FIGS. 6A-6D and FIGS. 7A and 7B. FIGS. 7A and 7B illustrate a method 700 that starts with a step 702 of providing a first wafer on which a flexible layer 322 (e.g., polyimide PI layer, see FIG. 6A, step b) is formed in step 704 (see also FIG. 6A, step a). The wafer may be a Si (100) wafer on top of which a 10 μm thick polyimide film (PI-2611) is coat spin. The various sizes, temperature and other parameters provided in these methods are for enabling one skilled in the art to make the system 300 or 500. However, those skilled in the art would understand that variations of these parameters are possible without affecting the efficiency of the invention. In other words, the present method is not intended to limit the invention with the specific values of the parameters noted herein.

In step 706, a soft bake of the PI layer at T=90° C. for 90 s is performed, followed by a second bake at T=150° C. for 90 s. Final curing is performed by ramping the hot plate temperature from 150° C. to 350° C. at a rate of 240°/hour, and leaving the first wafer to cure for 30 minutes at T=350° C. This step is shown in FIG. 6A, step c.

In step 708, a second Si (100) wafer is provided, on top of which a thin film of Au is sputtered (see FIG. 6B, steps 1 and 2). The Au film is used because it has low bonding energy with PDMS, and hence it will act as a good intermediate layer to ease the final release process. A first stretchable layer 320 is spin coated in step 710 on the second wafer (see FIG. 6B, step 3). The first stretchable layer 320 may be 100 μm thick PDMS (Sylgard 184™) and may be cured at T=90° C. for 30 minutes. The first stretchable layer will act as the bottom encapsulation layer of the outer layer 310. This step is then followed by a step 712 of $O_2$ plasma treatment for 2 mins, which will temporarily make the PDMS layer hydrophilic, to improve its adhesion to the subsequent layer.

In step 714, the PI layer 322 is peeled from the first wafer (see arrow between FIGS. 6A and 6B) and carefully transferred on top of the treated PDMS of the second wafer (see FIG. 6B, step 4). To pattern the PI layer 322, an Aluminum (Al) hard mask (see FIG. 6C, step 6) is used for its selectivity to PI etching gases. The PI layer is first treated with oxygen plasma at low power (30 W) for 2 mins in step 716 (see FIG. 6B, step 5). This step is applied to improve the adhesion of the metal films on top of the PI layer and avoid delamination issues. Then, in step 718, a first mask is formed on top of the PI layer 322, as illustrated in FIG. 6C, step 6. The first mask is obtained by sputtering 200 nm of Al. The first mask is patterned in step 720 as shown in FIG. 6C, step 7.

In step 722, another oxygen plasma is applied on top of the patterned PI layer (see FIG. 6C, step 8) and then the first metallic layer 324 (e.g., 10 nm/180 nm Titanium/Gold (Ti/Au) layers) is sputtered in step 724 on top of the patterned PI layer (see FIG. 6C, step 9). The first metallic layer 324 is then patterned in step 726 using a second mask (see FIG. 6C, step 10). The first metal layer includes, as discussed above with reference to FIG. 3, the bottom contacts of the pressure/depth sensors 304. In step 728, a pressure sensitive rubber layer is deposited (see FIG. 6C, step 11), which corresponds to the capacitive layer 326 in FIG. 3. This layer can be deposited as a 50 μm thick PDMS cured at T=75° C. for 75 minutes. A second metallic layer 330 (e.g., Ti/Au (10 nm/180 nm)) is then deposited in step 730 by repeating the steps 4 to 10 in FIGS. 6B and 6C, which were performed to create the first metallic layer 324. These repeated steps begin with a second transfer of another PI layer 328, all the way to the end by sputtering and patterning the second metallic layer 330 in step 732 (see FIG. 6C, step 12). This second metallic layer may include the top contacts of the depth sensors 304, the temperature sensors 302, as well as the conductivity/salinity sensors 306. More than two metallic layers may be built for this system.

The system-on-chip integration is performed in step 734 (see FIG. 6C, step 13), during which the power supply 314 and the computing device 318 are electrically connected to the second metallic layer. The built system is encapsulated in step 736 by adding a second stretchable layer 332, which connects to the first stretchable layer 320, so that the entire system 500 is encapsulated in PDMS. As previously discussed, the salinity sensor 306 in FIG. 3 needs to be in direct contact with the environment. Thus, a portion of the first or second stretchable layers (i.e., the PDMS encapsulation) is removed to form an opening for the salinity sensor(s) 306. Step 736 may be performed by spin coating a 150 μm thick PDMS and curing it at T=90° C. for 30 minutes (see FIG. 6C, step 14). In step 738 the completely packaged Marine Skin system 300 or 500 is released from the second wafer, for example, using a tweezer as illustrated in FIG. 6C, step 15. Note that the steps shown in FIGS. 7A and 7B may be performed in a different order. Also, some of the steps are optional. In other words, not all the steps shown in FIGS. 7A and 7B need to be performed to achieve the system 300 or 500.

The final system 300 or 500 is shown in FIG. 6D. Note that the system is mostly transparent, the various sensors are visible inside the system, the system is flexible (i.e., it can be bent to any angle) and stretchable (i.e., it can be stretched to change a selected size at least between 5 and 25% of the selected size).

Due to the advances in the art of miniaturized electronics applied in the method of FIGS. 7A and 7B, the system produced by this method is waterproof, ultra-lightweight (less than 2.4 grams in water), fully conforming (physically flexible and stretchable), standalone (wireless multi-sensory capable of measuring conductivity, temperature, depth) and very small (e.g., the entire system may measure 55 mm×55 mm×0.3 mm or less). This ultra-light weight and small multi-sensor system has non-invasive application, high performance multi-sensing, and constant data logging with significantly lower cost. The integrated arrays of temperature, pressure and conductivity sensors may simultaneously monitor the animal's diving patterns, and the surrounding environmental conditions.

The "Marine Skin" multi-sensor system discussed above is advantageous over the existing systems because it is physically flexible and stretchable, and displays multi-sensory capability with simultaneous sensing and selectivity. The system exhibits an ultra-thin net-shape construction, and can be easily integrated in an intimate fashion on curved animal surfaces, a quality which none of the existing system possess. The wavy network pattern of the metallic layers (see FIG. 6D) was designed for optimal two-dimensional expansion, with inherent elasticity and twisting capability, enabled through intrinsic PDMS elasticity and the geometry of thin metal routings. The packaged system dimensions shown in FIG. 6D are 55 mm×55 mm×0.3 mm. However, these sizes can be downscaled by decreasing the array size.

Thus, contrary to the existing marine tags that are generally constrained by the bulky size of their systems and packaging, the packaged system 300 or 500 is compact (21 mm×10 mm) and conformal (less than 4 mm in height; the system shown in FIG. 3 has a height of 3.5 mm). The system described above includes at least one of each of the temperature, pressure and salinity sensors. Those skilled in the art would understand that the system may be built to include large arrays of capacitive pressure sensors and resistive temperature detectors (RTD) incorporating individual salinity sensors based on electrodes separated by a given gap.

Various designs can be implemented to achieve a variety of sizes and elastic deformation. The "net" architecture shown in FIG. 2 allows the system to conform to the body of the animal and stretch/contract with their movements, ensuring comfort and adhesion under any circumstance. The fabrication process of this system is conducted using a low-cost CMOS compatible approach, allowing ease of scalability, batch fabrication, and precision. Detailed integration strategy of the "Marine Skin" system described with regard to method 700 shows compliant 3D integration of the SoC on top of the sensory array, accompanied with conformal encapsulation and release of the final flexible system.

The system discussed above has been tested under various conditions for evaluating the temperature, pressure and salinity sensitivity as for other factors. Effect of salts on electrode performance is important for marine systems development. Therefore, long term experiments (over 20 days) were performed to test the integrity of the encapsulation packet of the system. The test was conducted in Red Sea water (~40 PSU). The results indicated a durable flexible packaging.

Figure 8A:
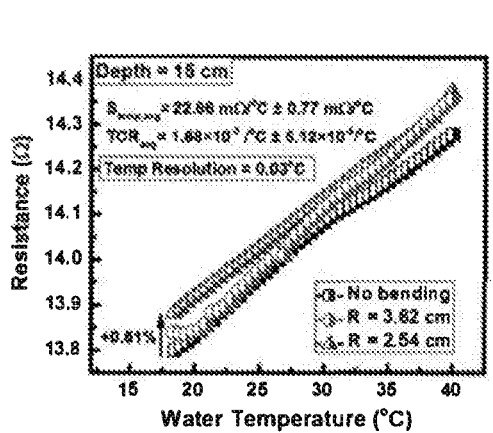
FIGS. 8A to 8F illustrate various characteristics of a multi-sensor system that is flexible and stretchable.
Figure 8B:
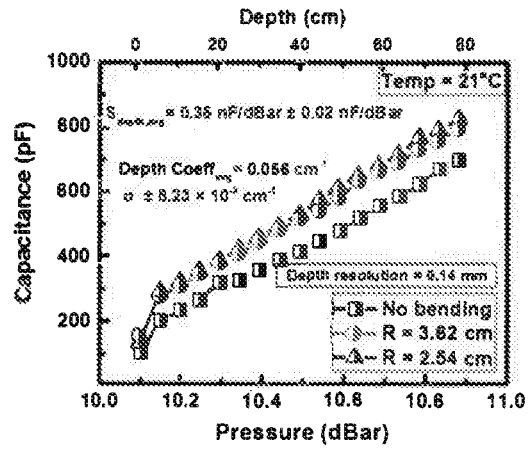
Figure 8C:
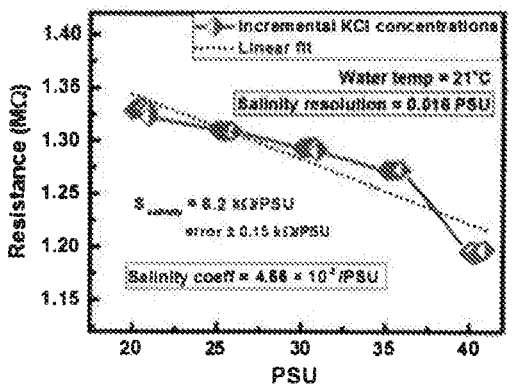
Figure 8D:
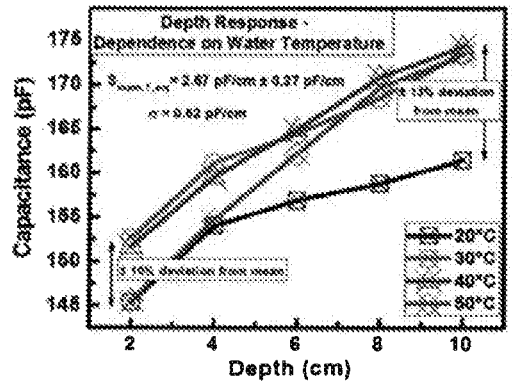
Figure 8E:
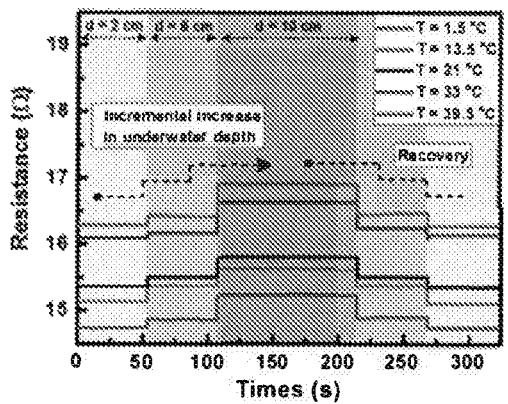
Figure 8F:
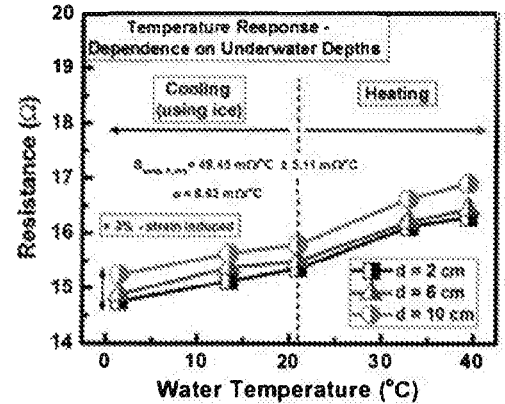

As the "Marine Skin" system is targeted for conformal placement on marine animals of irregular sizes and shapes, the sensors' functionalities need to be tested under diverse mechanical bending conditions to assess their performance and stability when employed on curved surfaces. Measurements were conducted in seawater (40 PSU) under varying depth and water temperatures, as illustrated in FIGS. 8A-8F. FIG. 8A shows the system's resistive response to water temperature variations under various bending conditions, FIG. 8B shows the capacitive response of the pressure sensor to increased underwater pressure/depth under various bending conditions, FIG. 8C shows the salinity response of the system to increase salinity, FIG. 8D shows the effect of the depth on the salinity sensor at various temperatures, FIG. 8E shows the dynamical resistance fluctuations of the system under difference thermal conditions, and FIG. 8F shows the effect of immersion on the temperature sensor's performance.

The temperature sensor's response in FIG. 8A, under different bending radii, shows that the sensor's sensitivity stayed intact with an average sensitivity of $S_{temp,\,avg}$=22.66 m$\Omega$/° C. and a temperature resolution of 0.03° C., sufficient to detect desirable fluctuations of 0.1° C. in the ocean's temperature. Minor strain-induced increase of 0.61% in absolute resistance value is observed under bending. The effect of strain would be generally greater. However, the implemented wavy design, along with the sensors' placement in the neutral plane of the packaging, minimizes stress and strain propagation in the structures.

Similarly, FIG. 8B show the pressure sensor's stability under different bending conditions, with an average linear sensitivity of $S_{depth,\,avg}$=0.35 nF/dBar=0.056 cm$^{-1}$, a standard deviation of $\sigma$±8.3×10$^{-4}$ cm$^{-1}$ attributed to variations in platform curvature, and an estimated high depth resolution of 0.14 mm. The testing setup was limited to an 80 cm depth range, which is considered shallow for marine tagging applications. For this depth range, the "Marine Skin" system's sensors display high resolution with great linearity, without any signs of signal saturation or attenuation. These findings show high performance functionality under higher pressures, and can be used to predict sensory behavior for extended depths.

Salinity detection was analyzed in FIG. 8C, which displays the measured resistance generated from the produced ion channel versus salinity levels. For water temperature of 21° C., salinity levels ranging from 20 PSU (practical salinity unit) to 41 PSU are respectively translated into conductivities from 29.56 mS/cm to 56.3 mS/cm. As salinity levels increase, the water solution becomes more conductive, and hence the resistance decreases. It is observed a fairly linear behavior of the sensor with a sensitivity of $S_{salinity}$=6.2 k$\Omega$/PSU=0.00466/PSU and a high salinity resolution of 0.016 PSU. These values make the salinity sensor capable of distinguishing slight variations in ecologically-relevant changes in ocean's salinity (see Talley (2002)). Response and recovery times were then analyzed through continuous logging at T=21° C. in incremental PSU solutions. For a fixed salinity of 20 PSU, a total response time was determined to be $t_{salinity\_response}$=38 s and a total recovery time of $t_{salinity\_recovery}$=45 s. In this regard, note that conductivity sensors are also sensitive to changes in water temperature and conditions, where thermal conductivity of water is $k_{water}$=0.611 W/m·K (see ChemWorx (2009)). Higher temperatures lead to faster ions movement in water, increasing the conductivity. However, because the present system also contains a temperature sensor, this information can be accounted for and calibrations can be performed in order to retrieve temperature-corrected salinity values.

The selectivity of the sensors towards changes in the marine environment is related to the sensor's performance. The plots in FIGS. 8D-8F show the effect of temperature variations on pressure sensitivity and the effect of depth on the water temperature sensitivity. Nevertheless, the "Marine Skin" system integrates sensory multifunctionality, with pressure and temperature values continuously being recorded and dependent on one another. Each sensor is highly selective to its targeted stimuli and no significant performance change was observed from cross-sensitivity via water temperature and depth variations. The observed disparities and strain-induced changes follow well-defined trends that can be easily compensated for.

The efficient lightweight system discussed in FIGS. 3 and 5 made it possible to perform underwater experiments for longer periods of time without hindering the animal's usual movement. The fully packaged Marine Skin system weights an incomparable<6 g in air and <2.4 g in water, and has a battery lifetime of up to 1 year assuming a logging rate of 2 s. Tests of the system integrity in seawater are illustrated in FIGS. 9A and 9B, which display continuous and repeatable responses.

Figures 9A, 9B:
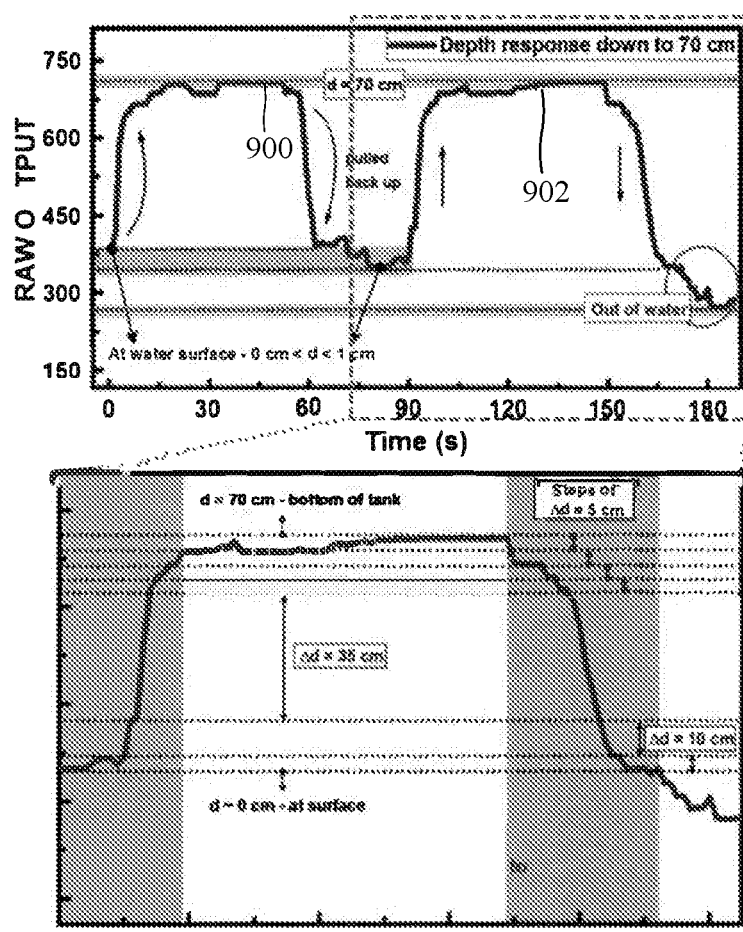
FIGS. 9A and 9B illustrate the response of a multi-sensor system that is flexible and stretchable as it moves up and down under water.

FIG. 9A shows a real-time logging plot over a period of 3 mins. The collected data shows the depth pattern 900 of immersing the system down to 70 cm and pulling it back up to the water surface (with depth 0 cm<$d_{surface}$<1 cm). The second repeated cycle 902 shows consistency in response and recovery, and hence repeatability. FIG. 9B highlights the small steps of $\Delta d$=5 cm that were performed as the system went down to 70 cm and back up to the surface. From 70 cm back to 50 cm, the 5 cm steps are well resolved since the time delay taken between each step is 1 s, whereas in other areas the sensory system was continuously moved without stopping it at defined depths.

Data retrieved from the system is denoted as "raw output," which corresponds to uncalibrated data directly retrieved from the capacitive sensing interface. In order to correlate the raw output to corresponding capacitance values, a calibration test was conducted, where the integrated system was used to measure already known capacitance values of off-the-shelf capacitors. The raw output was plotted as a function of the system's capacitance $C_{system}$, displaying a linear relationship that correlates "raw output" and readout capacitance values through a slope of 297.825 $pF^{-1}$. The retrieved equality is thereafter used to back-calculate system's capacitance and hence underwater depth values.

Data retrieval when the animals surface is appropriate for air-breathing animals (marine mammals and reptiles). For continuously submerged animals, the data can be collected by using a pop-up device (see Hoolihan (2011)).

Figure 10A:
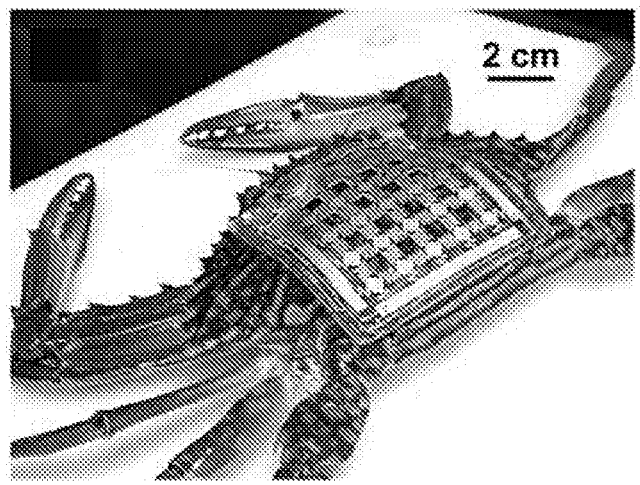
FIGS. 10A and 10B illustrate a multi-sensor system, which is flexible and stretchable, being attached to a crab and the response measured as the crab moves up and down in the water.

The system discussed above has been field tested on crustaceans—specifically on a swimming crab (*Portunus pelagicus*) captured along the east coast of the central Red Sea. The "Marine Skin" system was conformally and non-invasively attached on the crab's shell using superglue, as illustrated in FIG. 10A. For testing on a wider range of marine animals, especially mammals (e.g. dolphins), bio-compatible adhesives should be used as an alternative to superglue for a sturdy and non-invasive attachment method.

In this regard, according to an embodiment, a Scapa Soft-Pro® Skin Friendly Adhesive may be used. This adhesive is composed of a highly breathable double coated polyethylene film. One side is coated with an acrylic adhesive while the other side is coated with a silicone gel adhesive. The acrylic side would be placed in contact with the skin since it offers a strong, secure bond to skin and is ideal for long wear applications, whereas the silicone side would provide adherence to the silicone based PDMS packaging of the marine skin tag. This adhesive has a tattoo-like sheer feel and a secure fit around body contours. The system shows excellent adhesion when tested on human skin with long wear time of at least 4 days of aggressive underwater exposure in the Red Sea. Also, it is easily removable, minimizing skin trauma and discomfort to the marine animals.

Figure 10B:
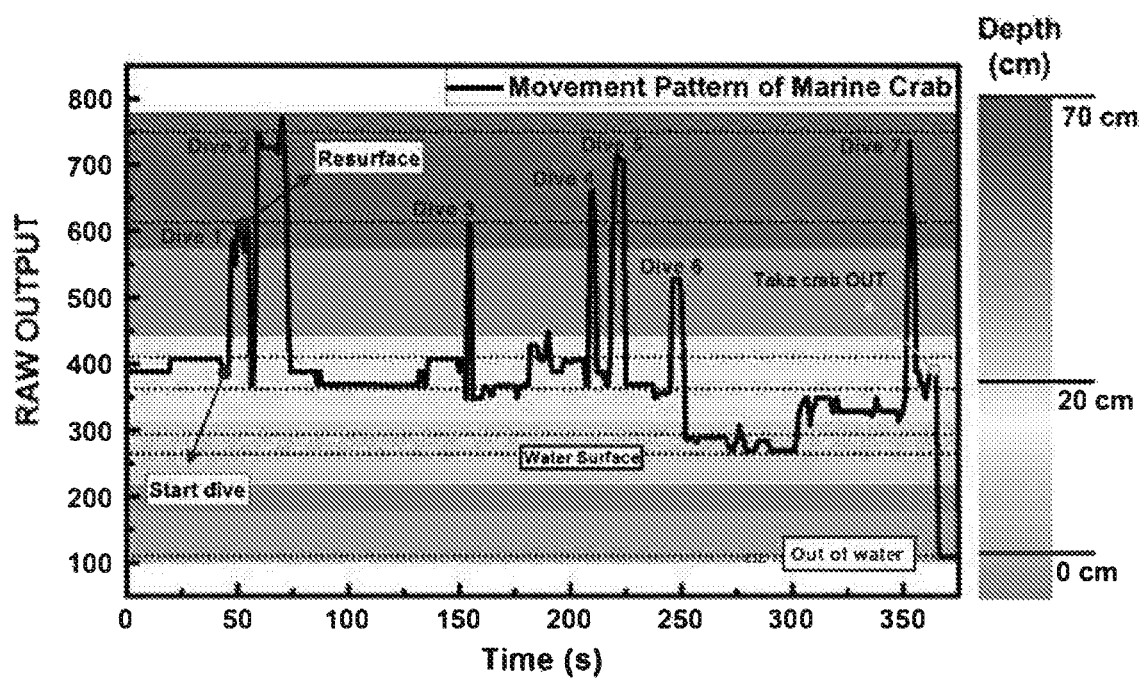

The crab to which the system was attached was monitored in sea water using a logging frequency of 1 Hz. The depth pattern logged is shown in FIG. 10B and depicts continuous and active tracking of the crab's diving and resurfacing patterns for 6 mins. Using a 1 Hz logging frequency, the system consumes low power, yielding an operation life of 5 months. Battery life can be further extended by optimizing the operating conditions and reducing sampling intervals. As for temperature logging, the current system can detect changes of 0.2 mV, which translates into 0.5° C. resolution. The portable system can be further optimized to detect changes of 0.437 μV, and hence improve the detection resolution up to 0.001° C., but this would translate into higher power consumption and the need for a bigger and heavier battery.

To put in perspective the advancements and possibilities created by the Marine Skin sensory system, the benchmark table illustrated in FIG. 1 compares the most notable developments in marine tags, including commercial and academic projects. Tags that exhibit similar functionalities to system 300 or 500 were compared, not only based on their form factor, weight, performance, and resolution, but also based on battery lifetime (hereafter referred to as Tag Deployment Lifetime "TDL"), which was normalized according to the respective sampling rate of each project. Performance or resolution never seems to be an issue with sensing based projects, since current technology advancements are used to come up with the best sensing solution. However, improving TDL and reducing form factor are the major challenges that require focus. The form factor has a significant effect on the underwater behavior and stress of tagged animals. Devices extruding off from an animal skin create drag, which forces marine animals to make extra effort in order to move, altering their natural behavior. The extra carried weight and tag design affect diving patterns, mating, nesting behavior, swimming drag, movement capacity, and performance ability of marine animals. Tagged marine animals are samples of a bigger population and the ecosystem as a whole, therefore the incorporation of telemetric devices should not alter their natural performance, behavior, physiology or survival.

When compared to the system illustrated in FIG. 1, the Marine Skin system overcomes this concern owing to its extremely lightweight design and compliant form factor made specifically to adapt to different animal sizes and shapes, while maintaining a long lifetime. In this regard, in one embodiment, the Marine Skin system has a length of 55 mm, a width of 55 mm, and a height of 3.5 mm, with the sensor patch having a height of 0.3 mm. The weight of the system in this embodiment is less than 6 g in air and about 2.4 g in water. The TDL in days is about 152 and the fastest possible sample is 5 ms. The temperature working range is about 1.5 to 40° C. with a temperature resolution of about 0.03° C. The depth range of the system was tested up to 80 cm (11 dBar) with a pressure resolution of 0.14 mm. The conductivity range is about 29.5 to 56.3 mS/cm and the salinity resolution is about 0.016 PSU. In contrast to this system, currently available solutions have proven to be unsuitable for tagging young specimens, invertebrates, or small species due to their rigid design, heavy weight and bulky form factor.

Therefore, compliant sensory systems (e.g., system 300 or 500) that are non-invasively attached to marine animals can enhance the quality of aquatic life while advancing scientific exploration. The present embodiments have shown a waterproof, flexible, stretchable, Bluetooth enabled standalone Marine Skin system capable of operating under vast pressure, temperature and salinity regimes. The system is easily adaptable to a diversity of animals of any size and shape. The system is focused on maintaining animal comfort and movement through a compliant and cost-effective design. Unlike anything else, the Marine Skin system is non-invasive and lightweight (e.g., less than 2.4 g), exhibiting a long deployment lifetime without compromising performance and resolution.

The disclosed exemplary embodiments provide methods and systems for monitoring various ocean parameters while the system is attached to a marine life organism. It should be understood that this description is not intended to limit the invention. On the contrary, the exemplary embodiments are intended to cover alternatives, modifications and equivalents, which are included in the spirit and scope of the invention as defined by the appended claims. Further, in the detailed description of the exemplary embodiments, numerous specific details are set forth in order to provide a comprehensive understanding of the claimed invention. However, one skilled in the art would understand that various embodiments may be practiced without such specific details.

Although the features and elements of the present exemplary embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

REFERENCES

Duarte, C. M. Global change and the future ocean: a grand challenge for marine sciences. Frontiers in Marine Science 1, 63 (2014).

Halpern, B. S. et al. A global map of human impact on marine ecosystems. Science 319, 948-952 (2008).

Block, B. A. et al. Tracking apex marine predator movements in a dynamic ocean. Nature 475, 86-90 (2011).

Costa, D. P., Breed, G. A. & Robinson, P. W. New insights into pelagic migrations: implications for ecology and conservation. Annual review of ecology, evolution, and systematics 43, 73-96 (2012).

Cooke, S. J. et al. Developing a mechanistic understanding of fish migrations by linking telemetry with physiology, behavior, genomics and experimental biology: an interdisciplinary case study on adult Fraser River sockeye salmon. Fisheries 33, 321-339 (2008).

Humphries, N. E., Weimerskirch, H., Queiroz, N., Southall, E. J. & Sims, D. W. Foraging success of biological Lévy flights recorded in situ. Proceedings of the National Academy of Sciences 109, 7169-7174 (2012).

Miller, K. M. et al. Genomic signatures predict migration and spawning failure in wild Canadian salmon. science 331, 214-217 (2011).

Bridger, C. J. & Booth, R. K. The effects of biotelemetry transmitter presence and attachment procedures on fish physiology and behavior. Reviews in Fisheries Science 11, 13-34 (2003).

Jepsen, N., Schreck, C., Clements, S. & Thorstad, E. in Aquatic telemetry: advances and applications. Proceedings of the Fifth Conference on Fish Telemetry held in Europe. Ustica, Italy. COISPA Technology and Research and Food and Agriculture Organization of the United Nations. FAO, Rome. 255-259.

Cooke, S. J. et al. Biotelemetry: a mechanistic approach to ecology. Trends in Ecology & Evolution 19, 334-343 (2004).

Brown, R. S., Cooke, S. J., Anderson, W. G. & McKinley, R. S. Evidence to challenge the "2% rule" for biotelemetry. North American Journal of Fisheries Management 19, 867-871 (1999).

Walker, K. A., Trites, A. W., Haulena, M. & Weary, D. M. A review of the effects of different marking and tagging techniques on marine mammals. Wildlife Research 39, 15-30 (2012).

Geraldi, N. R. & Powers, S. P. Subtle changes in prey foraging behavior have cascading effects in a shallow estuary. Marine Ecology Progress Series 427, 51-58 (2011).

Broderick, A. C. & Godley, B. J. Effect of tagging marine turtles on nesting behaviour and reproductive success. Animal behaviour 58, 587-591 (1999).

Alex Shorter, K., Murray, M. M., Johnson, M., Moore, M. & Howle, L. E. Drag of suction cup tags on swimming animals: modeling and measurement. Marine Mammal Science 30, 726-746 (2014).

Hammerschlag, N., Cooke, S. J., Gallagher, A. J. & Godley, B. J. Considering the fate of electronic tags: interactions with stakeholders and user responsibility when encountering tagged aquatic animals. Methods in Ecology and Evolution 5, 1147-1153 (2014).

Todd Jones, T. et al. Calculating the ecological impacts of animal-borne instruments on aquatic organisms. Methods in Ecology and Evolution 4, 1178-1186 (2013).

Broadbent, H., Ketterl, T., Reid, C. & Dlutowski, J. in OCEANS 2010. 1-7 (IEEE).

Broadbent, H. A CTD Biotag for Mid-sized Marine Predators Doctor of Philosophy thesis, University of South Florida, (2012).

SMRU-Instrumentation. CTD Oceanography SRDL (Argos), <http://www.smru.st-and.ac.uk/Instrumentation/CTD/>(2017).

Nassar, J. M., Rojas, J. P., Hussain, A. M. & Hussain, M. M. From stretchable to reconfigurable inorganic electronics. Extreme Mechanics Letters 9, 245-268 (2016).

Shaikh, S. F. et al. Freeform Compliant CMOS Electronic Systems for Internet of Everything Applications. IEEE Transactions on Electron Devices (2017).

Hussain, A. M. & Hussain, M. M. CMOS-Technology-Enabled Flexible and Stretchable Electronics for Internet of Everything Applications. Advanced Materials (2015).

Hussey, N. E. et al. Aquatic animal telemetry: a panoramic window into the underwater world. Science 348, 1255642 (2015).

Hooker, S. K. & Boyd, I. L. Salinity sensors on seals: use of marine predators to carry CTD data loggers. Deep Sea Research Part I: Oceanographic Research Papers 50, 927-939 (2003).

Talley, L. D. Salinity patterns in the ocean. The Earth system: physical and chemical dimensions of global environmental change 1, 629-640 (2002).

ChemWorx, A., Archives, C. & Photonics, A. Polymer data handbook. J. Am. Chem. Soc 131, 16330-16330 (2009).

Hoolihan, J. P. et al. Evaluating post-release behaviour modification in large pelagic fish deployed with pop-up satellite archival tags. ICES Journal of Marine Science: Journal du Conseil 68, 880-889 (2011).

What is claimed is:

1. A multi-sensor system for monitoring water parameters, the system comprising:
   a first metallic layer;
   a dielectric layer formed on the first metallic layer;
   a second metallic layer formed on the dielectric layer;
   a power source electrically connected to the second metallic layer;
   a computing device electrically connected to the second metallic layer;
   a stretchable outer layer that encapsulates the first metallic layer, the dielectric layer, the second metallic layer, the power source and the computing device; and
   a salinity sensor formed as two electrodes separated by a gap in the second metallic layer, wherein the two electrodes are exposed to an environment of the multi-sensor system,
   wherein the multi-sensor system is stretchable and flexible.

2. The system of claim 1, wherein a size of the multi-sensor system changes between 5 and 25% of an original length of the multi-sensor system.

3. The system of claim 1, wherein a weight of the multi-sensor system is less than 6 grams in air.

4. The system of claim 1, wherein a height of the multi-sensor system is between 1 and 4 millimeters.

5. The system of claim 1, wherein a length of the multi-sensor system is about 25 to 75 millimeters and a width of the multi-sensor system is about 25 to 75 millimeters.

6. The system of claim 1, wherein the stretchable outer layer is attached with glue to a marine life organism.

7. The system of claim 1, further comprising:
a first flexible layer formed between a first stretchable layer of the stretchable outer layer and the first metallic layer.

8. The system of claim 7, further comprising:
a second flexible layer formed between the dielectric layer and the second metallic layer.

9. The system of claim 8, wherein the first and second metallic layers each includes a first layer of gold and a second layer of titanium, the first and second flexible layers are formed of polyamide, and the stretchable outer layer is formed of an encapsulating material that is water proof, biocompatible, and soft.

10. The system of claim 1, further comprising:
a temperature sensor formed as a resistor in the second metallic layer.

11. The system of claim 1, further comprising:
a pressure sensor formed as a capacitor, wherein a first plate of the capacitor is formed in the first metallic layer, a second plate of the capacitor is formed in the second metallic layer, and a dielectric of the capacitor is the dielectric layer.

12. The system of claim 1, wherein
the first and second metallic layers are nets,
each of the nets is formed from a plurality of plates interconnected by metal having a serpentine shape,
the plurality of plates of the first and second metallic layers form, along with the dielectric layer, a plurality of pressure sensors, and
the metal having the serpentine shape in the second metallic layer forms a plurality of temperature sensors.

13. A multi-sensor system for monitoring water parameters, the system comprising:
first and second metallic layers interposed by a dielectric layer, wherein the first and second metallic layers are nets, each of the nets is formed from a plurality of plates interconnected by metal having a serpentine shape;
a plurality of temperature sensors for measuring a temperature of an ambient, wherein the metal having a serpentine shape in the second metallic layer forms the plurality of temperature sensors;
a plurality of pressure sensors for measuring a pressure of the ambient, wherein the plurality of plates of the first and second metallic layers form, along with the dielectric layer, the plurality of pressure sensors;
a salinity sensor for measuring a salinity of the ambient;
a computing device having,
a temperature sensing unit configured to read a temperature from the temperature sensor,
a pressure sensing unit configured to read a pressure from the pressure sensor,
a salinity sensing unit configured to read a salinity from the salinity
a memory configured to store the temperature, the pressure and the salinity, and
a low power Bluetooth transmitter configured to send the stored temperature, pressure and salinity to an external device; and
a power source for supplying power to the computing device,
wherein the multi-sensor system is stretchable and flexible.

14. A method of forming a multi-sensor system for monitoring water parameters, the method comprising:
forming a first metallic layer;
forming a dielectric layer on the first metallic layer;
forming a second metallic layer on the dielectric layer;
attaching a power source to the second metallic layer;
forming a salinity sensor as two electrodes separated by a gap in the second metallic layer, wherein the two electrodes are exposed to an environment of the multi-sensor system;
attaching a computing device to the second metallic layer; and
encapsulating in a stretchable outer layer the first metallic layer, the dielectric layer, the second metallic layer, the power source and the computing device,
wherein the multi-sensor system is stretchable and flexible.

15. The method of claim 14, wherein the multi-sensor system is stretchable when a size changes between 5 and 25% of an original length of the multi-sensor system under an applied force.

16. The method of claim 14, wherein a height of the multi-sensor system is between 1 and 4 millimeters.

17. The method of claim 14, further comprising:
attaching the stretchable outer layer with glue to a marine life organism.

18. The method of claim 14, further comprising:
forming a temperature sensor as a resistor in the second metallic layer; and
forming a pressure sensor as a capacitor, wherein a first plate of the capacitor is formed in the first metallic layer, a second plate of the capacitor is formed in the second metallic layer, and a dielectric of the capacitor is the dielectric layer.

19. The method of claim 14, wherein
the first and second metallic layers are nets,
each of the nets is formed from a plurality of plates interconnected by metal having a serpentine shape,
the plurality of plates of the first and second metallic layers form, along with the dielectric layer, a plurality of pressure sensors, and
the metal having the serpentine shape in the second metallic layer forms a plurality of temperature sensors.

* * * * *